United States Patent [19]

Skeirik

[11] Patent Number: 4,823,957
[45] Date of Patent: Apr. 25, 1989

[54] BRACKET TABLE COVER

[76] Inventor: Lewis Skeirik, 24 Central St., Georgetown, Mass. 01833

[21] Appl. No.: 143,338

[22] Filed: Jan. 13, 1988

[51] Int. Cl.$^4$ ............................ B65D 1/34; B65D 6/04
[52] U.S. Cl. .................................... 206/557; 206/63.5; 206/368; 206/369; 206/518; 206/567; 229/3.5 R; 229/DIG. 11
[58] Field of Search .................... 206/63.5, 368, 369, 206/440, 449, 518, 554, 567, 804, 557; 220/408, 409, 410; 229/3.5 R, DIG. 11

[56] References Cited

U.S. PATENT DOCUMENTS

| | | | |
|---|---|---|---|
| 896,432 | 8/1908 | Booth | 206/369 |
| 950,988 | 3/1910 | Booth | 206/369 |
| 959,534 | 5/1910 | Holtz | 206/369 |
| 979,493 | 12/1910 | Holtz | 206/368 |
| 1,123,830 | 1/1915 | Zincke et al. | 433/77 |
| 1,659,315 | 2/1928 | Dailey | 206/63.5 |
| 2,100,396 | 11/1937 | Heymann | 229/3.5 R |
| 2,704,974 | 3/1955 | Setman | 206/518 |
| 2,844,247 | 7/1958 | Jones | 206/518 |
| 2,866,584 | 12/1958 | Long | 220/417 |
| 3,346,957 | 10/1967 | Maurer et al. | 433/79 |
| 3,442,376 | 5/1969 | McDivit | 206/63.5 |
| 3,468,468 | 9/1969 | Foote | 229/3.5 R |
| 3,536,248 | 10/1970 | Odenhagen | 229/3.5 R |
| 3,997,101 | 12/1976 | Florian | 229/DIG. 11 |
| 4,502,599 | 3/1985 | Perelman | 206/554 |

OTHER PUBLICATIONS

Brochure "A-dec Over-the-Patient Delivery Equipment", by the A-dec Company, Newberg, Oregon.
Brochure "The Disposable Instrument Tray", of Preventative Systems Ltd., Roseville, Calif., 1979.

Primary Examiner—David T. Fidei
Attorney, Agent, or Firm—Morse, Altman, Dacey & Benson

[57] ABSTRACT

A stack of improved bracket table cover sheets for use by dentists is disclosed. The sheets have ridges throughout their peripheries. The outer edges of the ridges extend downwardly. The ridges are designed to fit snugly over the peripheral ledges of the bracket table or of a separate backing designed to be positioned on the bracket table. Preferably, one of the raised edges is provided with an integral flap. The improved bracket table cover sheet of the stack comprises a paper component and a water and organic solvent impervious component. In one form, the impervious component is wax that impregnates the paper component. In another form the impervious component is a polymeric coating. Each bracket table cover sheet of the stack is characterized by a drape, hand, and feel that permits it to be easily folded and wrapped into a disposable pack.

10 Claims, 1 Drawing Sheet

BRACKET TABLE COVER

BACKGROUND OF THE INVENTION

1. Field of the Invention

The present invention relates generally to bracket table covers for use at dental operating stations and, more particularly, to an improved bracket table cover, that is easier and safer to use than corresponding prior art products.

2. The Prior Art

Typically, a dental station features, in addition to a chair, what is known as a "bracket table." This bracket table is designed to keep dental instruments and materials conveniently accessible to the dentist while he is treating a patient sitting in the chair. A disposable bracket table cover, or a stack of disposable bracket table covers, may be superposed on the bracket table at any given time. Where a stack is used, the topmost bracket table cover is used. When the treatment of a patient is completed, all instruments are removed from the soiled bracket table cover, which then is discarded. A clean cover then is positioned and ready for the next patient.

On occasion, soiled instruments and/or materials, particularly, dental tissues, dental floss, and the like, contaminated by blood or saliva, come into contact with the edges of the bracket table, a bracket table cover and/or the edges of the bracket table covers of a stack. Unfortunately, the edges of the bracket table and/or the edges of the stack may be contaminated under such circumstances. If such an occurrence is noticed by the dentist, he then must desinfect the bracket table and/or discard the entire stack. Regretfully, if the dentist fails to notice or consider such soiling, infection control for subsequent patients is reduced or lost.

The following U.S. patents typify the prior art. U.S. Pat. No. 950,988, issued to C. F. Booth in 1910, discloses a removable tray designed for thorough cleansing at a location remote from the dentist's chair. U.S. Pat. No. 1,123,830, issued to E. Zicke et al in 1915, discloses a dental cabinet with a sanitary paper cover that can be drawn across its top from a roll. U.S. Pat. No. 1,659,315, issued to F. L. Dailey in 1928, discloses a sanitary, shaped-paper receptacle for dental use. U.S. Pat. No. 3,346,957, issued to J. A. Maurer et al in 1967, discloses a shaped, removable dental tray designed to be cleansed at a remote location. And U.S. Pat. No. 3,442,376, issued to P. A. McDivit in 1969, discloses a removable plastic implement mat for use in combination with a dental set-up tray, the mat being readily sterilizable. More recently, a plastic disposable, compartmentalized dental instrument tray has become available to dentists from Prevention System Ltd. of Roseville, Calif. This disposable tray contributes to an aseptic environment and reduces chances of cross contamination, but is relatively stiff and, therefore, not adapted to be folded or wrapped conveniently before being discarded. There is a need for an improved bracket table cover product that manifests the advantages, but not the disadvantages of the prior art.

SUMMARY OF THE INVENTION

It is a principal object of the present invention to overcome existing disadvantages by providing a stack of improved bracket table covers, which are inexpensive, yet simple and effective in use. More specifically, it is an object of the present invention to provide a stack of bracket table covers, essentially comprising a plurality of sheets of processed paper of particular configuration and composition.

The configuration is such that each of the sheets is provided throughout its periphery with an upwardly extending ridge having downwardly extending edges, a freely extending flap being formed in one section of the ridge. The ridge serves to prevent dental instruments from rolling beyond the edges, and to prevent contaminants from entering between the superimposed cover sheets in the stack. The flap formed in the ridge of each of the sheets facilitates the lifting and easy separation of the top soiled sheet from the rest of the stack. The peripheral ridges of the sheets are designed to fit snugly over the peripheral ledges of a bracket table, or the peripheral ledges of a separate tray designed to be positioned on the bracket table. As is well known, manufacturers of dental stations not only vary the shapes and construction of the dental chairs, but also vary the shapes and sizes of the bracket tables. Use of the separate tray is indicated in instances where standardization in the size of the bracket table covers is desirable or suggested by economic circumstances. Alternatively, the stack is provided with a shaped cardboard backing that maintains the shape of the sheets of the stack.

The composition of the sheets of the stack of bracket table covers of the present invention is such that each sheet exhibits soft and compliant "hand and feel." More specifically, each sheet, has barely enough dimensional stability to maintain its configuration by itself and sufficient drape to ensure that it can be rolled and folded tightly after use, thereby wrapping all disposable and/or soiled matter thereon into a small pack for easy disposal. In one form, each sheet is impregnated by a substance, such as paraffin wax, to isolate it antiseptically from its underlying sheet. In an alternative form, each sheet is provided at its upper face with a thin coating of a water and chemical solvent resistant polymer.

Other objects and advantages of the present invention will in part be obvious and will in part appear hereinafter.

The invention accordingly comprises the improved bracket table cover of the present disclosure, its component parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

In general, the purpose of the present invention is to provide infection control in dentists' offices in an efficacious and cost-effective manner.

Figure 1:
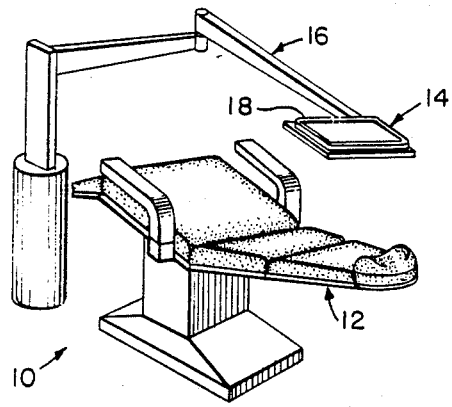
FIG. 1 is a perspective view of a dental operating station featuring a chair and a bracket table operatively mounted adjacent thereto.
Figure 3:
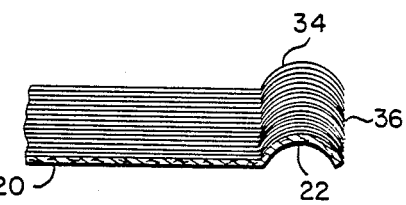
FIG. 3 is a broken-away cross-section of the stack of FIG. 2, taken along the line 3—3.

In FIG. 1, there is illustrated a dental operating station 10 featuring, inter alia, a dental chair 12 and a bracket table 14, which is mounted for both horizontal and vertical displacement adjacent the dental chair 12 via arms 16, as is well known. The bracket table 14, for example, is formed of stainless steel and is provided with ledges 18 throughout its periphery. Manufacturers have been known to vary the sizes of their bracket tables as well as the shapes and heights of their peripheral ledges. If a bracket table is of non-standard size it is contemplated by the present invention that a separate tray 20, of standardized dimensions as illustrated in FIG. 3, be provided with peripheral ledges 22 of standardized shape and height. The separate tray 20 is designed to be positioned on the bracket table 14. The tray 20 preferably is composed of a hard polymer, such, as for example, bakelite or the like. Alternatively, the separate tray is replaced by a stiff cardboard backing to which the stack is affixed, by which the stack is carried, and by which the stack maintains its predetermined configuration.

Figure 2:
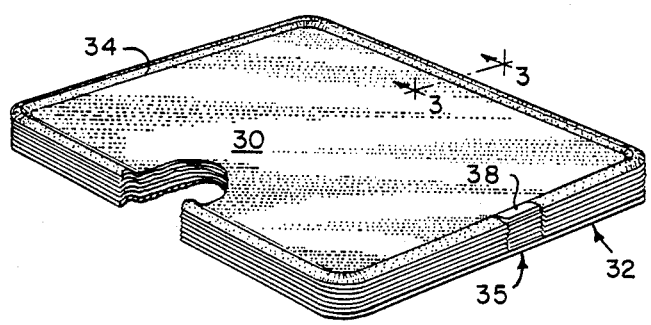
FIG. 2 is a perspective view of a stack, partly broken-away which is designed to be positioned on the bracket table shown in FIG. 1.

FIG. 2 illustrates a stack 32 of bracket table covers according to the invention, the top bracket table cover sheet of the stack being designated by 30. Each bracket table cover sheet 30 essentially comprises a stratum throughout its periphery with ridges 34 having downwardly extending outer edges 36. The significance of the ridges 34 with their downwardly extending outer edges 36 will be more fully described below, in particular with reference to FIG. 3. Each bracket table cover sheet 30, furthermore, is provided with a flap 38 at one point 35 in its peripheral ridge 34. The flap 38 is designed to facilitate the easy grasping and separation of the single uppermost bracket table cover sheet 30 from the stack 32. This aspect of the invention will also be more fully described below, in particular with reference to FIG. 6.

The stack 32 of bracket table covers sheets 30 is illustrated as being designed for seating on the bracket table 14. As mentioned earlier, in instances where the bracket table 14 is not of a standard size, the stack 32 will be disposed intermediately on the separate tray 22, which then is positioned on the bracket table 14. As may be observed, the ridges 34 of the bracket table cover sheets 30 are designed to fit sungly over the peripheral ledges 18 of the bracket table 14, or over the peripheral ledges 22 of the tray 20, as the case may be, and with their respective outer edges 36 extending downwardly. In any case, the stack 32 is backed so that it maintains the shape of the stack's sheets, the composition and construction of which will be described below.

Depending on the composition of the sheets of the stack 32, the stack may be shaped as an entity in a suitable die, or the individual sheets may be shaped and then stacked. In operation, the reversal in the direction of ridges 34 ensures that no contaminants, whether from soiled instruments or other materials placed on the top bracket table cover sheet 30, can enter between adjacent cover sheets in the stack 32. The chances of cross contamination are thereby markedly reduced. The ridges 34 serve as well to prevent instruments from rolling beyond their periphery and to keep the underlying bracket table 14 clean.

Figure 4:
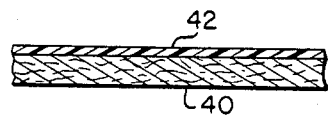
FIG. 4 is an enlarged and exaggerated, broken-away, cross-section, illustrating the construction and composition of one embodiment of a bracket table cover sheet incorporating the present invention.

FIG. 4 illustrates a preferred construction of the plurality of sheets of the stack. In FIG. 4, the sheet 30 is shown as including a paper substrate 40 and a thin coating 42 of a water and chemical solvent resistant polymer such as mylar or teflon. The thin coating 42 provides the imperviousness needed to achieve infection control. Preferably, the thin coating 42 is no greater than one mil (0.001") thick, say from 0.0001 to 0.001 inch thich, and the substrate 40 is no greater than three mils (0.003") thick, say from 0.001 to 0.003 inch thick. Typically, the paper substrate 40 is composed of a porous soft and compliant fibrous, felted cellulosic of the type commonly used in the manufacture of tissue and napkins.

Figure 5:
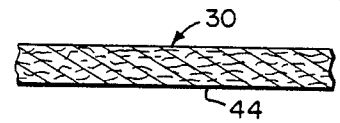
FIG. 5 is an enlarged and exagerated, broken-away, cross-section, illustrating the construction and composition of another embodiment of a bracket table cover sheet incorporating the present invention.

In FIG. 5, the sheet 30 is shown as a sheet of paper 44 that has been impregnated with a moisture and organic solvent impervious substance during its formation. One such, substance is paraffin wax, namely a solid, crystalline hydrocarbon mixture derived from the paraffin distillate portion of crude petroleum.

The invention also contemplates a bracket table cover sheet which incorporates both an impregnated paper base and a thin polymeric coating on its face, both materials being, for example, as above described.

Figure 6:
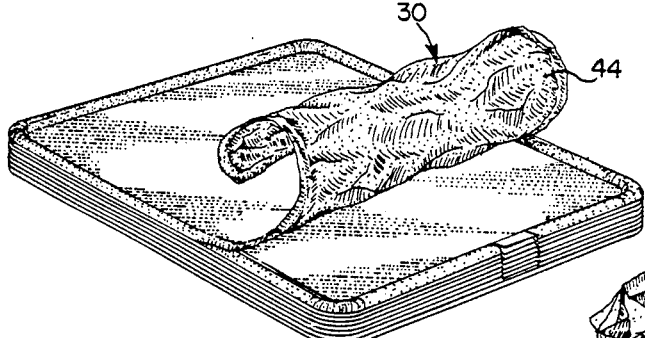
FIG. 6 is a perspective view similar to that of FIG. 2, but illustrating the folding and wrapping of the soiled top sheet of the stack into a self-contained disposable pack.
Figure 7:
FIG. 7 is a perspective view of the wrapped pack formed as in FIG. 6.

FIGS. 6 and 7 illustrate the operational use of the stack 32 of bracket table cover sheets of the invention. FIG. 6 illustrates the manipulation of the top soiled bracket table cover sheet 30 by folding it away from the stack 32 as at 44. Either the dentist or his assistant first catches the upwardly bent flap 38 of the top bracket table cover sheet 30 at one edge and proceeds to fold the sheet 30 away from that edge toward the opposite edge. He continues the folding and wrapping process until, as indicated in FIG. 7, a wrapped pack 46 is formed and ready for disposal. Of course, all instruments first will have been cleared from the top cover sheet 30 before folding.

As the top bracket cover sheet 30 is removed, the underlying cover sheet 30 becomes accessable. A typical stack 32 ranges from ¼ inch to ¾ inch in thickness. The thinness and modulus of flexure of each sheet are such that, when handled individually, it exhibits substantial drape, and clearly is unable to maintain its original shape.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. For use at a dental operating station, a bracket table cover comprising:
   (a) a sheet including a base paper component impregnated with a water and organic solvent impervious component;
   (b) said sheet being provided throughout its periphery with a ridge having downwardly depending outer edges;
   (c) said sheet being no greater than three mils thick;

(d) said ridge being provided with a flap.

2. The bracket table cover of claim 1 wherein said impervious component is paraffin wax.

3. The bracket table cover of claim 1 wherein said sheet is provided with a thin coating of polymer no thicker than one mil and wherein said polymer is selected from the class consisting of mylar and teflon.

4. For use at a dental station, a stack of bracket table cover sheets, each comprising:
  (a) a compliant and deformable base paper component impregnated with a water and organic solvent imperious component;
  (b) each being provided throughout its periphery with a ridge having downwardly depending outer edges, said ridges being provided with a flap;
  (c) each being no greater than three mils thick; and
  (d) a rigid backing for said stack, said rigid backing being a shape corresponding to the shape of each sheet, said backing being composed of a relatively stiff cardboard.

5. The stack of claim 4 wherein each of said plurality of sheets is impregnated with wax.

6. The stack of claim 5 wherein each of said plurality of sheets is provided with a coating on one face thereof, said coating being selected from the class consisting of mylar and teflon.

7. The stack of claim 6 wherein said backing is substantially like said sheet in extent and has ridges that are substantially like the ridges of said sheet.

8. The stack of claim 7 wherein said backing is composed of a polymer.

9. The stack of claim 7 wherein said backing is composed of metal.

10. For use at a dental operating station, a bracket table cover comprising:
  (a) a sheet including a base paper component and a water and organic solvent impervious component;
  (b) said impervious component being a thin coating of polymer no greater than one mil thick;
  (c) said sheet being provided throughout its periphery with a ridge having downwardly depending outer edges;
  (d) said sheet being no greater than three mils thick;
  (e) said ridge being provided with a flap.

* * * * *